US00PP21164P2

(12) United States Plant Patent
Blom

(10) Patent No.: US PP21,164 P2
(45) Date of Patent: Jul. 13, 2010

(54) ***CHRYSANTHEMUM* PLANT NAMED 'ZANMUSUNDOWN'**

(50) Latin Name: ***Chrysanthemum×morifolium* Ramat.**
Varietal Denomination: Zanmusundown

(75) Inventor: Wilhelmus Bernardus Blom, Leimuiden (NL)

(73) Assignee: Chrysanthemum Breeders Association Research B.V., Valkenburg (NL)

( * ) Notice: Subject to any disclaimer, the term of this patent is extended or adjusted under 35 U.S.C. 154(b) by 0 days.

(21) Appl. No.: 12/314,959

(22) Filed: Dec. 19, 2008

(51) Int. Cl.
*A01H 5/00* (2006.01)

(52) U.S. Cl. ..... Plt./289

(58) Field of Classification Search ..... Plt./289
See application file for complete search history.

*Primary Examiner*—Kent L Bell

(57) ABSTRACT

A *chrysanthemum* plant named 'Zanmusundown' characterized by its medium sized blooms with yellow ray florets and prolific branching; natural season flower date October 6–10; blooming for a period of 5 weeks.

3 Drawing Sheets

BACKGROUND OF THE INVENTION

The present invention relates to a new and distinct cultivar of *chrysanthemum* plant, botanically known as *Chrysanthemum×morifolium* Ramat., and hereinafter referred to by the cultivar denomination 'Zanmusundown'. 'Zanmusundown' is a product of a breeding and selection program for outdoor pot mums (garden mums) which had the objective of creating new *chrysanthemum* cultivars with a double type inflorescence, a natural season flower date starting at October 6–10; blooming for a period of 5 weeks. 'Zanmusundown' is a seedling resulting from the crossing of the female parent id 2824 and male parent id 4678. Plants of 'Zanmusundance' differ from plants of the parents in ray-floret color; that of the seedling is yellow, while that of the female parent is white, and of the male parent pink.

The new and distinct cultivar was discovered and selected as a flowering plant by Wilhelmus Bernardus Blom on a cultivated field in Rijsenhout, The Netherlands in 2004. The first act of asexual production of 'Zanmusundown' was accomplished when vegetative cuttings were used from the initial selection in 2004 and propagated further in a controlled environment in Rijsenhout, The Netherlands. The new cultivar has been found to retain its distinctive characteristics through successive propagations.

BRIEF DESCRIPTION OF THE DRAWINGS

The present invention of a new and distinct variety of *chrysanthemum* is shown in the accompanying drawings, the color being as nearly true as possible with color photographs of this type.

DESCRIPTION OF THE INVENTION

Figure 1:
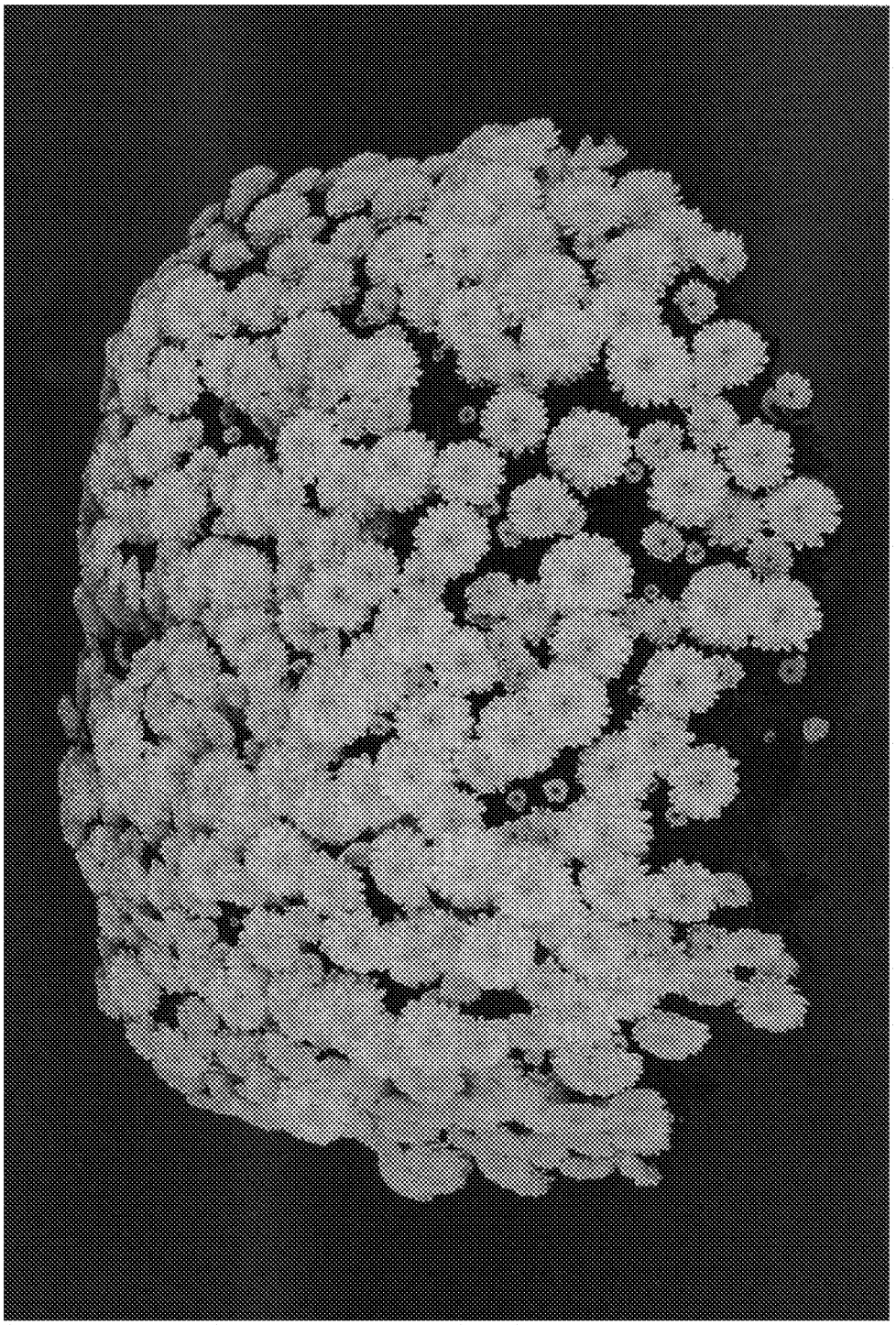
FIG. 1 shows a plant of the cultivar in full bloom.
Figure 2:
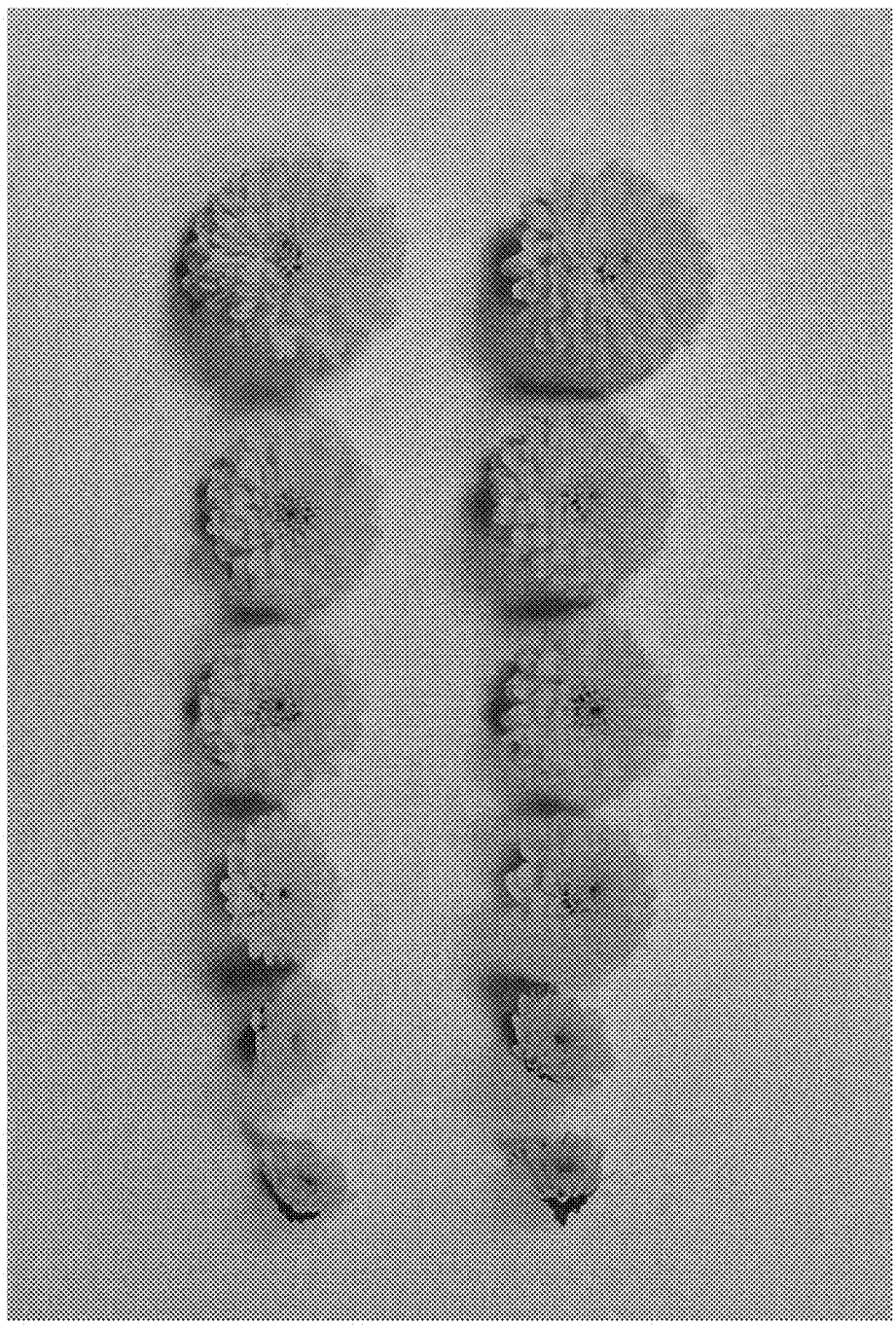
FIG. 2 shows the various stages of bloom of the new cultivar.
Figure 3:
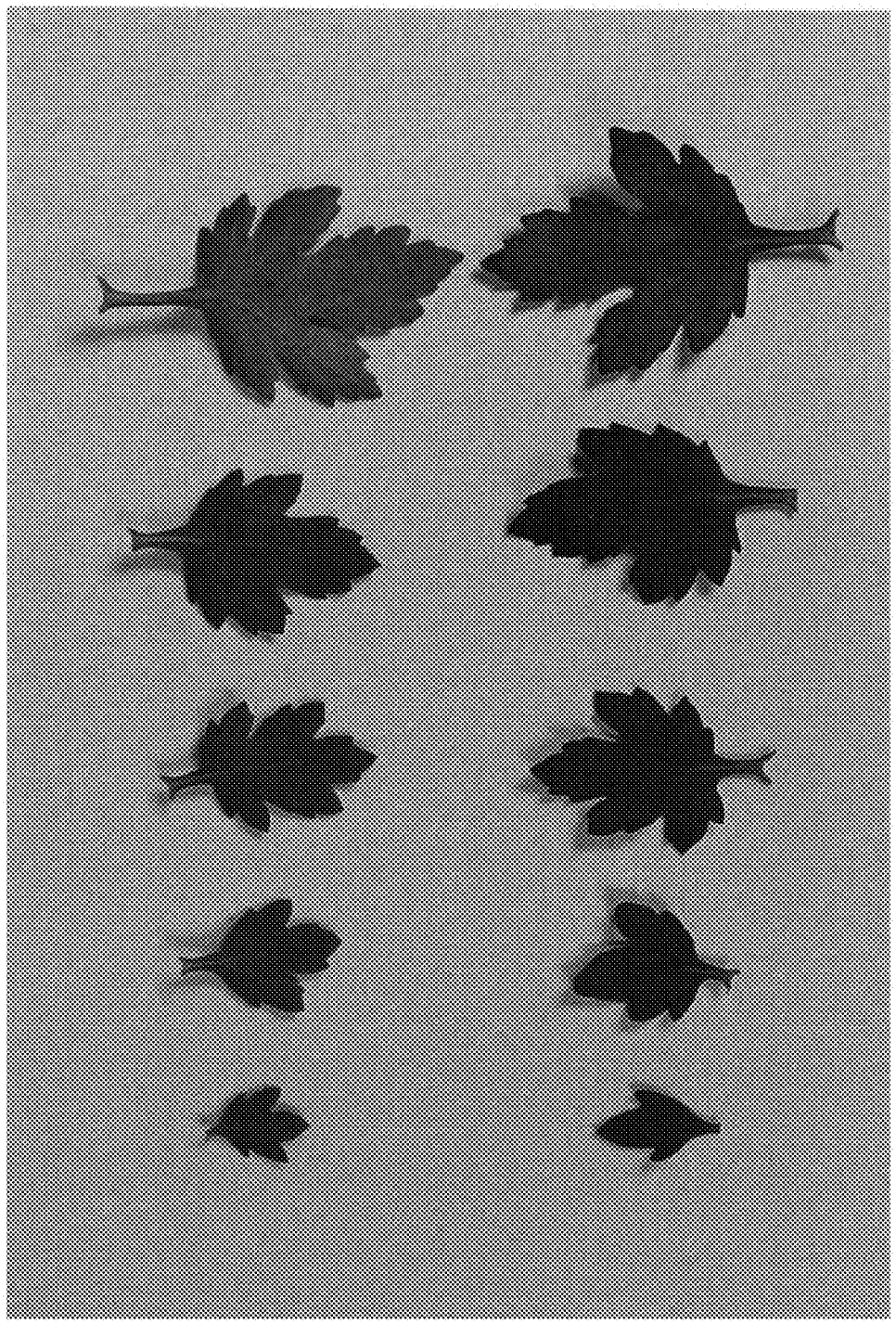
FIG. 3 shows the various stages of foliage of the new cultivar.

The observations and measurements were gathered from plants grown out door in Rijsenhout, The Netherlands under natural day length and temperature and planted in week 22 in 2008. The natural blooming date of this crop was October 6–10. The average height of the plants was 25 cm. No growth retardants were used. No tests were done on disease or insect resistance or susceptibility. No tests were done on cold or drought tolerance. This new variety produces medium sized blooms with yellow ray florets blooming for a period of 5 weeks.

From the cultivars known to inventor the most similar existing cultivar in comparison to 'Zanmusundown' is 'Zanmusundance' (U.S. Plant patent application Ser. No. 12/314,958). When 'Zanmusundance' and 'Zanmusundown' are being compared the following differences are noticed: The difference of 'Zanmusundance' and 'Zanmusundown' (1) Plant size. And (2) Flower color (1) The plants of 'Zanmusundance' are larger than those of 'Zanmusundown' (2) The flowers of Zanmusundance' are more soft yellow than those of 'Zanmusundown'.

The following is a description of the plant and characteristics that distinguish 'Zanmusundown' as a new and distinct variety.

The color designations are taken from the plant itself. Accordingly, any discrepancies between the color designations and the colors depicted in the photographs are due to photographic tolerances. The color chart used in this description is: The Royal Horticultural Society Color Chart, edition 2001.

TABLE 1

Botanical Description of *Chrysanthemum xmorifolium* Ramat. 'Zanmusundown'

| | |
|---|---|
| Bud | |
| Size | Small; cross-section 0.5 cm, height 0.4 cm |
| Shape | Oblate |
| Texture | Pubescent |
| Outside Color | Greyed-green 191A |
| Phyllaries | |
| Number | 50, arranged in 3 rows |
| Shape | Elliptic |
| Apex | Acute |
| Base | Truncate |
| Margin | Entire |

TABLE 1-continued

| Botanical Description of *Chrysanthemum xmorifolium* Ramat. 'Zanmusundown' | |
|---|---|
| Color | Upper side: Greyed-green 191A<br>Lower side Greyed-green 191C |
| Length and width | 4 mm; 1 mm |
| Texture | Pubescent |
| Inflorescence | |
| Type | Double |
| Height | 1.7 cm |
| Diameter | 4.5 cm |
| Peduncle length | 5 cm |
| Peduncle color | Green 139B |
| Peduncle diameter | 1 mm |
| Peduncle surface | Pubescent |
| Numbers per branch | Approx. 8 inflorescences |
| Flowering period individual inflorescence | Ca.4 weeks |
| Seeds | Produced in small quantities, ovate, Greyed-brown 199A, length 1.5 mm diameter 0.8 mm |
| Fragrance | Faint *chrysanthemum* odor |
| Color | |
| Center of inflorescences (ray-florets) | Immature stage: Yellow-orange 15A<br>Mature stage: Yellow-orange 15A |
| Color of upper surface of the ray-florets | Yellow 12A |
| Color of the lower surface of the ray-florets | Yellow 3B |
| Tonality from Distance | A garden mum with yellow inflorescences |
| Color of the ray-florets after aging of the plant | Yellow 12C |
| Ray florets | |
| Texture | Upper and lower side smooth |
| Number | 150 |
| Shape | Elliptic |
| Apex | Rounded |
| Base | Attenuate |
| Cross-section | Flat |
| Longitudinal axis of majority | Straight |
| Length of corolla tube | 5 mm |
| Ray-floret margin | Entire |
| Ray-floret length | 1.7 cm-2 cm |
| Ray-floret width | 6 mm |
| Ratio length/width | Medium |
| Disc florets | |
| Disc diameter | 1-2 mm |
| Distribution of disc florets | Scarce, only visible in mature bloom |
| Shape | Tubular |
| Color | Yellow 11D at apex, Yellow-green at 150D at base |
| Number | Ca. 4-5 |
| Length | 0.5 mm |
| Diameter | 0.3 mm |
| Receptacle | |
| Shape | Conical raised |
| Height | 3 mm |
| Diameter | 4 mm |
| Color | Green 138C |
| Reproductive Organs | |
| Androecium | Present in disc florets only |
| Stamen length | 3 mm |
| Stamen color | Yellow-green 144A |
| Anther color | Yellow 3A |
| Pollen | Small amount produced |
| Pollen | Yellow 12 A |

TABLE 1-continued

| Botanical Description of *Chrysanthemum xmorifolium* Ramat. 'Zanmusundown' | |
|---|---|
| Gynoecium | Present in both ray and disc florets |
| Style color | Yellow-green 154C |
| Style Length | 3 mm |
| Stigma color | Yellow 3A |
| Stigma Width | 1 mm |
| Ovary | Enclosed in calyx |
| Plant | |
| Form | Grown as a potmum, outdoor raised and mounded |
| Growth habit | Spherical shape |
| Growth rate | Low |
| Height | 25 cm |
| Width | 40 cm |
| Stem Color | Greyed-brown 199A |
| Stem Strength | Weak |
| Stem Brittleness | Brittle |
| Stem Anthocyanin Coloration | Not observed |
| Internode length | 1-2 cm |
| Length of lateral branch | From top to bottom 19 cm |
| Lateral branch color | Green 137 C |
| Lateral branch diameter | 2-3 mm |
| Lateral branch brittleness | Brittle |
| Branching (average number of lateral branches) | Prolific with 10 breaks after pinching |
| Natural season blooming date | October 6-10 to November 10-14 |
| Foliage | |
| Leaf color | Upper side: Green 139B<br>Lower side: Green N138B to N138C |
| Color midvein | Upper side: Yellow-green 147D<br>Lower side: Yellow-green 148D |
| Size | Small.; length 1.5-6 cm, width 2-3.5 cm |
| Quantity (number per lateral branch) | 16-18 |
| Shape | Elliptic |
| Texture upper side | Sparsely pubescent |
| Texture under side | Pubescent |
| Venation arrangement | Palmate |
| Shape of the margin | Entire to serrated |
| Shape of Base of Sinus Between Lateral Lobes | Rounded |
| Margin of Sinus Between Lateral Lobes | Diverging |
| Shape of Base | Attenuate |
| Apex | Mucronulate |
| Petiole length | 0.5-1.5 cm |
| Petiole diameter | 2-3 mm |
| Petiole color | Yellow-green 147D |

TABLE 2

| Differences with the comparison variety | | |
|---|---|---|
| | 'Zanmusundown' | 'Zanmusundance' |
| Plant height | 25 cm | 30 cm |
| Plant width | 40 cm | 45 cm |
| Color inflorescences disc | Yellow-orange 15A | Yellow 13A |
| Color upper side ray-florets | Yellow 12A | Yellow 9A |

I claim:

1. A new and distinct variety of *chrysanthemum* plant as described and illustrated.

* * * * *